United States Patent
Luyckx et al.

(12)

(10) Patent No.: US 7,064,109 B2
(45) Date of Patent: Jun. 20, 2006

(54) PHARMACEUTICAL COMPOSITION BASED ON MACROLIDES FOR TOPICAL APPLICATION IN OPHTHALMOLOGY

(75) Inventors: Jacques Luyckx, Ceyrat (FR); Frederic Pilotaz, Chamalieres (FR)

(73) Assignee: Laboratories Thea, Clermont-Ferrand (FR)

( * ) Notice: Subject to any disclaimer, the term of this patent is extended or adjusted under 35 U.S.C. 154(b) by 0 days.

(21) Appl. No.: 10/474,811

(22) PCT Filed: Apr. 11, 2002

(86) PCT No.: PCT/FR02/01263

§ 371 (c)(1),
(2), (4) Date: May 12, 2004

(87) PCT Pub. No.: WO02/083178

PCT Pub. Date: Oct. 24, 2002

(65) Prior Publication Data

US 2004/0197340 A1 Oct. 7, 2004

(30) Foreign Application Priority Data

Apr. 12, 2001 (FR) ................................. 01 05114

(51) Int. Cl.
*A61K 31/70* (2006.01)
(52) U.S. Cl. .......................... 514/29; 536/7.4
(58) Field of Classification Search .................. 514/29; 536/7.4
See application file for complete search history.

(56) References Cited

FOREIGN PATENT DOCUMENTS

| EP | 0925789 | 6/1999 |
|---|---|---|
| GB | 1152644 | 5/1969 |
| WO | 0057866 | 10/2000 |

OTHER PUBLICATIONS

Arthur H. Kibbe, "Handbook of pharmaceutical excipients, 3$^{rd}$ edition," ALPHA, Washington XP002187260, p. 329-p. 331.
Arthur H. Kibbe, "Handbook of pharmaceutical excipients, 3$^{rd}$ edition," ALPHA, Washington XP002187261, p. 362-p. 364.

*Primary Examiner*—Elli Peselev
(74) *Attorney, Agent, or Firm*—Millen, White, Zelano & Branigan, P.C.

(57) ABSTRACT

The invention relates to a pharmaceutical composition for preventing and/or treating eye infections, which is to be used by local application. It is in particular directed towards such a composition which is in the form of an eye lotion which can be distributed by drops, in which an antibiotic of the macrolide class, such as azithromycin, is in solution in an oily vehicle. This vehicle is, in particular, of the type of product essentially consisting of medium-chain triglycerides in which the alcohol functions of the glycerol are entirely esterified by carboxylic acids made from saturated hydrocarbons, the molecule of which comprises from 5 to 12 carbon atoms. They are preferably linear-chain fatty acids comprising from 8 to 10 carbon atoms, such as caprylic acid or capric acid. The composition is advantageously prepared by dissolving the active agent in the oily vehicle at a temperature not exceeding 70° C.

30 Claims, No Drawings

PHARMACEUTICAL COMPOSITION BASED ON MACROLIDES FOR TOPICAL APPLICATION IN OPHTHALMOLOGY

This application is a National Phase application of International application PCT/FRO2/01263 filed Apr. 11, 2002 and claims priority of French application 01/05114 filed Apr. 12, 2001.

The present invention relates to a novel pharmaceutical composition for preventing and treating eye infections, which is suitable for use by local application into the eye. As essential active principle, it comprises an antibiotic of the macrolide family, which it proposes to provide in the pharmaceutical form of an eye lotion, which can be distributed drop by drop.

It has already been known for a long time that macrolides are antibiotics which are particularly effective, including against eye infections. They are compounds of natural or more or less synthetic origin, the formula of which comprises a heterocycle which integrates a lactone function, generally associated with saccharide groups.

The basic example of macrolides is erythromycin, in which the heterocycle with a lactone function of the molecule already has 14 ring-members. Antibiotic efficacy has been verified not only for erythromycin itself, but also for many compounds which derive from its structure through various substituents on the main ring. In this respect, mention may be made of clarithromycin, roxithromycin and dirithromycin, for 14-membered rings, but also compounds such as spiramycin or josamycin, in which the cyclization coupling two substituents produces a 16-membered lactone ring.

Azalides represent a more recent group in the macrolide class. They derive from the basic structure of erythromycin by insertion of an intracyclic nitrogen into the ring with a lactone function. The leading member of this subclass of antibiotic macrolides is azithromycin, corresponding to N-methyl-11-aza-10-deoxo-10-dihydroerythromycin. In this compound, since the hydroxyl groups of positions 11 and 12 of the erythromycin are not substituted, the ring with a lactone function becomes a 15-membered ring. It is particularly common in the dihydrate form, which is not at all limiting, however, since the compound may also, conventionally, be in the form of any biologically compatible salt, as in the case of the other compounds of the class.

As with all compounds which can be used in ophthalmology, the pharmaceutical industry has worked to make it possible to use macrolides by local application rather than by general administration and, as regards application into the eye, the eye lotion form immediately comes to mind. However, the attempts in this respect have come up against difficulties which the present application aims to resolve. Reference may, in particular, be made to the document of the prior art consisting of international patent application WO 00/57866 (Insite Vision). This document recalls general knowledge regarding the properties of mucus membranes, the diseases and pathogenic agents which fall within the province of ophthalmic treatment and the conditions for administration of antibiotics, and it details various macrolide formulae, focusing mainly on azithromycin and on the conditions for the use thereof. While showing themselves to be anxious to treat eye diseases by local application of an azalide, the inventors exemplified previously azalide in the form of a suspension in water to which a suspending polymer has been added or in the form of an ointment. The same criticism is to be made with respect to the compositions in the form of azithromycin suspensions which are described in European patent application EP 0925789 (Pfizer).

The present invention makes it possible to avoid the drawbacks which result therefrom, in particular from the point of view of the risks of irritation of the mucus membranes of the eye and of the cornea. It is also directed towards, more generally, improving the conditions of use of the antibiotic compounds of the macrolide family in the uses thereof in ophthalmology. Thus, facilitating the penetration of the active agent into the cornea and the connective tissues of the eye, improving the retention thereof and the persistence time, ensuring that, at the concentration required as a function of the active dose to be administered at each instillation, the product does not cause any eye irritation, decreasing the number of daily instillations and the duration of the treatment and, generally, more fully satisfying the various requirements of medical practice, including while preserving the advantages of local administration, are among the intentions of the present invention. From this point of view, an objective of the invention is also, in particular, to ensure that the treatment is convenient, to facilitate administration of the composition and to avoid any blurred vision which may appear subsequent to topical application. The invention is also directed towards improving the conditions for industrial production of the medicinal products, in particular with regard to costs, and also the shelf life of the product before use.

Given these objectives, and others which may be more clearly understood from the remainder of the present description, the invention proposes a pharmaceutical composition suitable for the treatment of eye infections by local application, characterized in that it is in the form of an eye lotion containing, as therapeutically active agent, an antibiotic compound of the macrolide class in solution in an oily vehicle.

It applies especially advantageously to azalides, and more particularly to azithromycin. The latter compound currently appears to be the best for the purpose of the invention. Consequently, all the particularities of the invention which will be specified hereafter, will be so, unless otherwise indicated, accepting that the active principle for which they are most suitable from the industrial point of view is azithromycin, where appropriate as the standard compound of the azalide class.

The use of an oily vehicle rather than an aqueous medium, as has been proposed to date, makes it possible to ensure complete dissolution of the active principle at useful concentrations. A liquid is obtained which is a true solution, in regard of which it is distinguished from a suspension, as fine as the particles in suspension might be, even though the solution may have very variable viscosities. In addition, whatever the technique among those which it has been possible to envisage for dissolving macrolides in various media, problems of instability of the solution, easily envisaged as being particularly essential for compositions intended to be used by local application into the eye, and also as representing a bridle to an industrialization in good conditions, are encountered, in particular in the case of azalides.

One of the main advantages in having a true solution lies in the fact that the active principle is then applied homogeneously over the entire surface of the eye, whereas, in the case of a suspension, there is uneven contact of the particles of active compound on the eye. In addition, azalides are virtually insoluble in water, and also in tears, and solid particles thereof are therefore more readily removed from the eye by the tears, hence a short persistence time for compositions in the form of aqueous suspensions.

In combination with the complete solubilization of the macrolide in the vehicle according to the invention, the properties inherent to the oily nature of the vehicle also contribute to increasing the persistence time of the composition in the eye. Specifically, an oily film forms over the surface of the eye, which is less readily removed by the tears than in the case of an aqueous composition.

The formulation of the composition according to the invention in the form of an oily eye lotion also has other advantages. In particular, it engenders virtually no blurred vision, contrary to what should be expected of a composition which, moreover, has the advantage of an improved persistence time due to the oily vehicle. Now, it is known, for example, that other pharmaceutical forms commonly used for topical application in ophthalmology, such as ointments and creams, cause blurred vision for a relatively long period of time after administration.

The invention also relates to a process for preparing a pharmaceutical composition suitable for local application in ophthalmology, characterized in that it consists in dissolving the antibiotic compound in an oily vehicle, advantageously in the absence of other constituents, such as those known to be used in other contexts for promoting the dissolution of a product, also advantageously without adding secondary agents, such as various emulsifiers, thickeners or preserving agents.

According to the secondary characteristics of the invention, the active compound is dissolved in the oily vehicle either at normal temperature, which is generally preferable, if only to simplify the conditions for carrying out the process and to limit the cost thereof, or with slight heating, in particular to a temperature of between 30° C. and 90° C., and preferably of about 50 to 80° C., or more particularly of about 70° C., in particular when the active compound is azithromycin. In fact, the active compounds specified according to the invention prove to be not only virtually insoluble in water, but also heat-sensitive, and it is important to operate at a temperature at which the active principle remains stable.

A vehicle of relatively low viscosity will most commonly be chosen, in order to also be able to sterilize the solution, under the same temperature conditions, during a second step of the process, consisting in operating, for this, by filtration, and preferably at a cold temperature, as for the dissolving. One of the major interests of the invention is observed here, since the solution may, for example, be sterilized simply and effectively through a filtering membrane which has pore sizes of at most equal to 0.2 µm, and preferentially of between 0.1 and 0.2 µm, which it would not be possible to envisage in the case of suspensions.

This is particularly advantageous in the present case of the heat-sensitive molecules, namely the macrolides, or more especially the azalides, since the compositions in which they are contained cannot be sterilized by conventional means employing heating to high temperatures, for instance by autoclaving. Similarly, exposure to gamma-radiation, another method commonly used for sterilizing compositions comprising certain antibiotics, causes degradation of macrolides, and it is therefore preferable to avoid this.

In general, the concentration of the active agent in the oily vehicle may be very variable, depending on the particular active compound, within a range from 0.1 to 2% by weight of the total weight. However, as it has been possible to verify most particularly in the case of azithromycin, the invention has the advantage of producing solutions which are stable at relatively high concentrations of active principle, which leads to preference being given, for reasons of treatment efficacy, to concentrations of between 0.7 and 2%, in particular of about 1 to 1.5% by weight of the total weight.

In the context of the preferred embodiments of the invention, the oily vehicle used as excipient which is the solvent for the antibiotic active compound also corresponds to one or more of the secondary characteristics mentioned below, which may advantageously be applied simultaneously or in any technically effective combination.

Thus, the oily vehicle is preferably chosen so as to be a fatty oil which is of plant origin, but which is refined and/or hydrogenated and has a viscosity at normal temperature of less than 100 mPa.s (i.e. 100 cPo). This satisfies not only conditions suitable for eye lotions, as regards convenience of distribution drop by drop, but also particularly advantageous conditions for industrial production.

It is also desirable for the viscosity of the final composition to be at least 10 mpa.s at normal temperature, in particular for reasons of persistence on the cornea of the eye. In practice, the preferred viscosities are between 10 and 50 mPa.s, particularly about 20 to 40 mPa.s, at least when the aim is to simplify as much as possible the method for producing the medicinal product. Specifically, industrial production using sterilization carried out cold on the solution of the macrolide in the oil, without requiring the slightest heating, is then preferred.

It is evident that this does not prevent it possibly being useful, for particular cases of application, to supplement the pharmaceutical composition obtained by adding thereto a thickener compatible with the conditions of administration of the final product. For this, those skilled in the art will be able to find, within the industry, thickeners which they will use under sterile conditions in order to increase the viscosity without destroying the solution (mention should be made, for example, of cetyl acid, stearic acid, or derivatives thereof). A "delayed" effect of gradual and sustained release of the active principle is obtained by modulating the viscosity of the solution in this way, without, however, losing sight of the fact that, in accordance with the invention, it must be possible to instil it easily in the form of drops.

Other advantageous particularities of the oily vehicle suitable for the implementation of the invention are rather of the chemical type. The corresponding requirements are particularly well satisfied by the fatty oils commonly called medium-chain triglycerides. According to standards imposed by the European pharmacopoeia, these oils are extracted from coconut and consist essentially, for at least 95%, of triglycerides of the saturated fatty acids caprylic acid and capric acid. They are therefore, in turn, said to consist of caprylic/capric triglycerides or triglyceryl caprylate/caprate.

The composition thus obtained by dissolving the macrolide in a vehicle consisting of medium-chain triglycerides is particularly suitable for ophthalmic treatment by local application, since it makes it possible, inter alia, to satisfy one of the objectives of the invention, namely ensuring that the risk of irritation of the eye tissues by the composition is reduced to a minimum. The "irritation" includes all effects of temporary burning, of stinging or tears, which may be caused by the vehicle used in the formulation or by compounds which are associated with it. This is all the more important since the presence of tears in the eyes, as a result of an irritation, increases the rate of elimination of the antibiotic composition.

In the context of the invention, it therefore appears to be entirely advantageous to use medium-chain triglycerides, which have the particularity of being very well-defined chemically, and of not being associated with by-products which may cause irritation by contact with the eye. In addition, given the solubility of the antibiotic macrolides used in this oily vehicle, the composition according to the invention has the advantage of not requiring the addition of additives, such as suspending polymers, which considerably reduces the risk of irritation of the eye tissue. For the same reason, the oily solvent consisting of medium-chain triglycerides is, according to the invention, largely preferable to lanolin, which may also be mentioned for dissolving the macrolides, but which has the drawback of being irritant for the eye.

In the context of the implementation of the invention, the advantageous results of these characteristics of medium-chain triglycerides are better control of the composition of the formulation, a reduction of the side effects which may be engendered by irritant additives, and also better control of the industrial production of the eye lotion.

More generally, in the context of the implementation of the invention, the oily vehicles are chosen from fatty oils of plant origin which can be made available industrially and which consist essentially, in particular, of at least 80% (and preferably at least 95%), of fatty acid triglycerides. They are preferably compounds in which the three alcohol functions of the glycerol are esterified by the acid functions of fatty acids, the latter preferably being carboxylic acids made from saturated hydrocarbons. In addition, the oily vehicle used as solvent for the active compound in accordance with the invention is advantageously selected so that such triglycerides constituting it essentially derive from one or more acids made from hydrocarbons of medium molecular weight having a carboxylic acid function at the end of a linear chain. The acid molecule is therefore preferentially of medium length. From this point of view, it in particular comprises from 5 to 12 carbon atoms, and preferably from 8 to 10 carbon atoms, which is, in particular, the case of caprylic acid and capric acid.

The oily vehicle preferentially used for the formulation of the invention has a very low degree of unsaturation. Conventionally, the degree of unsaturation of an oil can be determined by the amount of halogen that can be bonded by the multiple bonds. The amount of halogen bonded, expressed in terms of iodine molecules per 100 g of oil, is known as the iodine number. Thus, the oily vehicle according to the invention preferably has an iodine number of less than or equal to 1. The oily vehicle preferentially used for the formulation of the invention has, moreover, a density advantageously between 0.9 and 1, and preferentially close to 0.95. According to other particularities of the invention, its refractive index is preferably between 1 and 2, preferentially between 1.3 and 1.5, and in particular about 1.45, and its density is advantageously close to 1, in particular between 0.9 and 1.

According to a preferred embodiment of the invention, the active therapeutic agent is azithromycin at a concentration preferably between 0.7 and 2% by weight, and preferentially between 1 and 1.5% by weight. The oily vehicle according to the invention makes it possible to completely solubilize azithromycin at these concentrations, which is particularly advantageous with respect to the aqueous vehicles. Indeed, while means for solubilizing azithromycin in aqueous compositions, for example in citric acid/salt compound mixture (as envisaged in European patent application EP 1 075 837 in the name of SIFI), are conventionally known, it has been noted by the present inventors that azithromycin is relatively unstable in this type of solution.

Quite advantageously, it is, on the contrary, very stable in the oily solutions of plant origin according to the invention.

According to a particular formulation of the invention, the pharmaceutical composition is preferentially intended to be provided in single-dose bottles. This is intended to mean a packaging which is disposable after the first use, containing the amount of product which can be used for two instillations, one into each eye. Due to the stability of the compositions of the invention, it is then advantageous not to add any additive to the solution, and in particular not to add any preserving agent.

However, according to another embodiment of the invention, the pharmaceutical composition comprises a preserving agent, as has been indicated above. This solution is generally preferred when the product is packaged in multidose bottles. The preserving agent is preferentially phenoxyethanol, phenylethyl alcohol, chlorobutanol, a quaternary ammonium salt, or any other preserving agent suitable for an eye lotion. In the latter case, when the formulation is prepared, the quaternary ammonium compounds, such as benzalkonium chloride, are preferentially incorporated while hot, and the concentration thereof preferentially does not exceed 0.01% by weight. Preserving agents of the paraben type are incorporated in the same way. They are, in particular, methyl and/or propyl and/or butyl parahydroxybenzoates.

According to a preferred preparation process of the invention, the pharmaceutical composition is sterilized by filtration, advantageously over a membrane with a porosity of between 0.1 and 0.2 µm. This operation may be carried out cold, more exactly at normal temperature, or with slight heating to a temperature of about 30 to 40° C., or to a temperature which is higher but remains lower than 80° C., for example a temperature of about 70° C. The latter solution may be preferred, in particular when the dissolution of the active compound in the oily vehicle is also performed hot, in which case the same temperature conditions may be used for the sterilization. However, when the viscosity of the oily vehicle chosen allows it, it generally appears to be preferable to perform the sterilization by filtration at normal temperature, for reasons of convenience and of cost. Various types of membrane may be used for this filtration operation, such as those based on cellulose acetate, on polyvinylidene fluoride (PVDF), on polyethersulphone (PES) or on polytetrafluoroethylene (PTFE).

To complete the description of the characteristics of the invention, and also that of the advantages and results thereof, some examples of preparation of the medicinal product according to the invention, which, of course, are not limiting, will now be considered. The active principle is present in the form of a base, without salification of the amine function. Comparative examples of the efficacy of the medicinal product according to the invention, compared to two other azithromycin-based medicinal products, are also provided, as is an example of ocular pharmacokinetics for azithromycin-based compositions according to the invention at various concentrations of active principle.

EXAMPLE 1

An eye lotion based on azithromycin at 1.5% by weight is prepared, with the centesimal formulation:

| | |
|---|---|
| azithromycin | 1.5 g |
| medium-chain triglycerides | Q.S. for 100 g |

The oily vehicle used corresponds to the European pharmacopoeia definition for a refined fatty oil containing 95% of medium-chain triglycerides in which the alcohol functions of the glycerol are entirely esterified by carboxylic acids made from saturated hydrocarbons, the chain of which is linear and of medium length, namely essentially capric acid and/or caprylic acid.

A mass of medium-chain triglycerides (MCTs) corresponding to 99% of its normal final mass is heated to 70° C. in a water bath. The azithromycin powder is dissolved in the triglycerides with stirring. The mixture is maintained at 70° C. for a few minutes, and then the solution obtained is left to cool to ambient temperature. The solution is then adjusted for weight with the MCT, and the mixture is finished off for a few minutes with stirring.

The azithromycin remains in solution after cooling, and the solution obtained is clear and limpid. It is subjected to sterilization treatment which is performed by filtration. The procedure is carried out at normal temperature. The filtration is carried out in sterile surroundings, over a filter with a 0.2 µm mesh, made of a polyethersulphone membrane. A true solution is obtained, which does not require, as in the case of formulations of macrolides in an aqueous vehicle, the addition of suspending polymers.

Stability studies, carried out at 25° C. and 60% humidity, and at 40° C. and 75% humidity, show that the solution obtained remains stable over time, for a period of more than six months.

EXAMPLE 2

An eye lotion based on azithromycin at 1% by weight, intended to be packaged in single-dose bottles, is prepared.

The centesimal formula thereof is as follows:

| | |
|---|---|
| azithromycin | 1 g |
| medium-chain triglycerides | Q.S. for 100 g |

The procedure in Example 1 is carried out in order to prepare the eye lotion of azithromycin in a medium-chain triglyceride vehicle, except that the concentration is taken to 1% by weight of the total weight of the composition. The solution is sterilized by filtration as in Example 1. For the medium-chain triglyceride fraction selected in the present example, the product has a viscosity of 30 mPa.s (30 cPo at 20° C.). It has a density of 0.95. It has a refractive index equal to 1.45. This value is very close to that of tears, which is equal to 1.33 in a healthy individual. It results therefrom that the risk of causing blurred vision during the instillation of the eye lotion into the eye is minimized.

EXAMPLE 3

An eye lotion based on azithromycin at 1% by weight, comprising a preserving agent, is prepared. This eye lotion, intended to be packaged in multidose bottles, has the following composition expressed by weight for 100 g:

| | |
|---|---|
| azithromycin | 1.5 g |
| benzalkonium chloride | 0.01 g |
| medium-chain triglycerides | Q.S. for 100 g |

A mass of MCT triglycerides corresponding to 99% of its normal final mass is heated to 70° C. in a water bath. The azithromycin and benzalkonium chloride powders are dissolved in the MCT with stirring. The mixture is kept at 70° C. for a few minutes, and is then left to cool to ambient temperature. The solution is then adjusted for weight with the MCT, and the mixture is finished off for a few minutes with stirring. The solution is then filtered, in sterile surroundings, over a 0.2 µm filter of the high flow rate type made of a polyethersulphone membrane.

EXAMPLE 4

An eye lotion based on azithromycin at 0.5% by weight, intended to be packaged in single-dose bottles, is prepared by carrying out the procedure as described in Example 1.

The centesimal formula thereof is as follows:

| | |
|---|---|
| azithromycin | 0.5 g |
| medium-chain triglycerides | Q.S. for 100 g |

By way of comparison, an aqueous composition of azithromycin at 1% by weight is prepared by dissolving azithromycin in hydrochloric acid. The pH of the solution is adjusted to 7.1 with tris(hydroxymethyl)aminomethane.

The solution is stored in the dark under temperature and humidity conditions of, respectively, 40° C. and 75%. Samples are taken from the solution at various time intervals and analysed by high pressure liquid chromatography in order to observe the degradation of the azithromycin over time. For the aqueous solution, degradation of the molecule begins to be seen after approximately four weeks, and this then accelerates to reach approximately 80% of degraded compound after two months.

On the other hand, as regards the composition according to the invention, studied under the same conditions, the azithromycin remains stable even after storage for 6 months. The solution remains limpid and transparent.

EXAMPLE 5

An eye lotion based on azithromycin at 0.5% by weight, comprising a preserving agent, is prepared. This eye lotion, intended to be packaged in multidose bottles, has the following composition, expressed by weight for 100 g:

| | |
|---|---|
| azithromycin | 0.5 g |
| benzalkonium chloride | 0.01 g |
| medium-chain triglycerides | Q.S. for 100 g |

A mass of MCT triglycerides corresponding to 99% of its normal final mass is heated to 70° C. in a water bath. The azithromycin and benzalkonium chloride powders are dissolved in the MCT with stirring. The mixture is kept at 70° C. for a few minutes, and is then left to cool to ambient temperature. The solution is then adjusted for weight with the MCT, and the mixture is finished off for a few minutes with stirring. The solution is then filtered, in sterile surroundings, over a 0.2 µm filter of the high flow rate type made of a polyethersulphone membrane.

EXAMPLE 6

An eye lotion based on roxithromycin, at a dose of 0.5% by weight, is prepared by carrying out the procedure as in the previous examples. The composition comprises a preserving agent since it is intended to be packaged in multidose bottles.

| roxithromycin | 0.5 g |
| benzalkonium chloride | 0.01 g |
| medium-chain triglycerides | Q.S. for 100 g |

EXAMPLE 7

An eye lotion based on clarithromycin, at a dose of 0.5% by weight, intended to be packaged in multidose bottles, is prepared.
The centesimal composition is as follows:

| clarithromycin | 0.5 g |
| chlorobutanol | 0.5 g |
| medium-chain triglycerides | Q.S. for 100 g |

A mass of commercial medium-chain triglycerides (MCTs) corresponding to 99% of its normal final mass is heated to 70° C. in a water bath. The clarithromycin powder is dissolved in the MCT with stirring. The mixture is kept at 70° C. for a few minutes, and is then left to cool to a temperature of 40° C. The chlorobutanol is then added and the stirring is maintained until complete cooling is reached. The weight is adjusted with the MCT and the mixture is finished off for a few minutes with stirring. The solution is finally filtered, in sterile surroundings, through a 0.2 μm filtering polyethersulphone membrane.

EXAMPLE 8

An eye lotion based on erythromycin, containing 0.5% by weight of erythromycin, is prepared by carrying out the procedure as in the previous example. Since the eye lotion is intended to be packaged in single-dose bottles, no preserving agent is added.

EXAMPLE 9

An eye lotion based on erythromycin at 0.5% by weight is prepared, corresponding to the following centesimal composition:

| erythromycin | 0.5 g |
| chlorobutanol | 0.5 g |
| medium-chain triglycerides | Q.S. for 100 g |

The procedure is carried out as in the previous examples. The solution obtained is limpid. It has a viscosity of about 30 mpa.s at normal temperature. The product is marketed in single-dose bottles for distribution drop by drop, applied into the eye.
As a variant, in this example as in the previous ones, the viscosity may be modulated to values possibly ranging, for example, up to 100 mpa.s by adding a thickener which is miscible in the MCT to the solution.
Higher viscosities can be produced, but here, it is preferred to conserve sufficient fluidity for the solution to be suitable as an eye lotion and for the formation of the drops not to be hindered.

EXAMPLE 10

An eye lotion prepared according to Example 2 is subjected to pharmacokinetic tests in order to examine the bioavailability of the medicinal product in the eye. The measurements are taken from the conjunctiva, from the cornea and from the tears of the eyes of rabbits, in comparison with two other azithromycin-based preparations. The azithromycin level is measured several times a day for six days after administration of a single initial dose.
Three formulae are thus tested. The first concerns an oral dose of azithromycin concentrated at 20 mg/kg, administered by taking a tablet. The second concerns a dose into the eye of an aqueous suspension of azithromycin concentrated at 1% by weight, administered locally by instilling a drop of the suspension at the surface of the rabbit's eye. The third concerns the oily solution prepared in accordance with Example 2, which is administered in the same way.
The results on the conjunctiva show that the first formula, namely the oral dose of azithromycin, does not make it possible to exceed a conjunctival concentration of azithromycin of greater than 0.1 μg/g, whereas the other two formulae produce significant levels 24 hours after administration, which are 0.55 μg/g for the aqueous formula and 0.60 μg/g for the oily formula of the invention. The superiority of the latter emerges especially with regard to the prolonging of the presence of a minimum mean azithromycin level. This level is indeed greater than 0.25 μg/g (minimum level for eliminating microorganisms) for only one day for the form in aqueous suspension, whereas, for the oily form (eye lotion prepared according to Example 2), it remains greater than 0.25 μg/g over a period of three days.
Regarding the cornea, the oral dose only becomes detectable after 72 hours, to reach 0.25 μg/g after six days. The aqueous suspension leads to levels of about 3 μg/g one day after instillation, which decrease so as to drop to 0.6 μg/g six days after instillation. The oily solution proves to be clearly superior; the azithromycin concentration reaches 3.8 μg/g 24 hours after instillation and remains above 1 μg/g six days later.
Besides the fact that the azithromycin exhibits very clear corneal tropism, the formulation of the eye lotion prepared according to Example 2 is particularly suitable for optimal delivery of the active principle in this ocular region. In the case of the cornea, the topical use of azithromycin proves to be more effective for rapidly delivering the active principle to its site of action.
Regarding the tests in tears, the lachrymal levels of azithromycin are still microbiologically significant one day after instillation. The lachrymal levels are 1.9 μg/g for the aqueous suspension and 2.0 μg/g for the oily solution. They are insufficient for the oral dose, the presence of azithromycin being undetectable in this case.

EXAMPLE 11

The formulations prepared according to Examples 1 and 4 are subjected to a study of ocular pharmacokinetics in humans.
The tests consist in instilling a drop of eye lotion onto the surface of the eye of patients at one or more given moments, and then taking tear samples from the treated eyes at various time intervals.
The samples taken are analysed by high pressure liquid chromatography coupled to mass spectrometry, in order to determine their azithromycin content. The results thus obtained correspond to the concentration of azithromycin in the tears at each sampling time. It is verified that the concentration of azithromycin in the tears is at least equal to 0.5 μg/g in order to obtain the desired therapeutic effect. This value corresponds to the minimum inhibitory concentration of azithromycin generally described as being the minimum concentration necessary to obtain therapeutic effectiveness in the eyes, for all sensitive microorganisms. Thus, the concentration of azithromycin and the persistence time of the composition must be sufficiently high, in relation to one another, for a dose of antibiotic greater than or equal to the minimum inhibitory concentration (MIC) to be delivered to the eye tissues targeted.

Lachrymal Kinetics After Administration of a Single Drop of Eye Lotion:

For each formulation, the lachrymal concentration of azithromycin is measured 0.5; 1; 2; 4; 8 and 24 hours after administration of a drop at the surface of the eye.

For the eye lotion containing 0.5% of azithromycin, the concentration of azithromycin in the tears is less than 0.85 µg/g, the value corresponding to the minimum quantification threshold of the assay method, this being for all the samples, including those taken very early, within one hour following administration.

Regarding the eye lotion containing 1.5% of azithromycin, the following lachrymal concentrations are obtained:

| Time (hours) | [Azithromycin]/tears (µg/g) |
|---|---|
| 0.5 | 8.85 |
| 1 | 4.53 |
| 2 | 2.45 |
| 4 | 1.68 |
| 8 | 0.87 |
| 24 | 0.91 |

It may be noted here that azithromycin is still found in the tears, at a level very largely greater than 0.5 µg/g, 24 hours after administration of a single dose of eye lotion at 1.5%.

Satisfactory results were also observed for a concentration of azithromycin in the eye lotion of 1%, a concentration of azithromycin of about 1 to 1.5% thus appearing to be suitable for delivering a therapeutically effective concentration in humans.

Lachrymal Kinetics After Repeated Administration of the Eye Lotion:

This study consists in assaying azithromycin in the tears, as previously, but after administration of several drops of eye lotion at regular time intervals.

The eye lotion here contains 1.5% of azithromycin. A first drop is administered at time 0, and then another at each of the following times: 12; 24; 48 and 72 hours. Tear samples are taken 72; 96; 120 and 144 hours after the first administration.

The following concentrations of azithromycin are obtained in the tears:

| Time (hours) | [Azithromycin]/tears (µg/g) |
|---|---|
| 72 | 2.53* |
| 96 | 2.98 |
| 120 | 5.61 |
| 144 | 2.14 |

*Value obtained before administration of the drop at 72 hours.

After five successive applications of the 1.5% azithromycin solution of Example 1, distributed over a period of 3 days (i.e. 72 hours), a high concentration of azithromycin is still found in the tears 6 days (i.e. 144 hours) after the first administration.

The above description clearly explains, in particular with the aid of the detailed examples which have just been set out, how the invention proceeds, in a way which those skilled in the art could not predict, to achieve the objectives which it set itself. In particular, it clearly emerges from the above results that a limited number of instillations of the composition containing 1 or 1.5% of azithromycin according to the invention makes it possible to obtain lachrymal concentrations which are clearly higher than the minimum inhibitory concentration over a relatively long period of time and, through the pharmacokinetic profiles obtained in humans, that it is particularly suitable for treating bacterial eye infections using an administration regime consisting of a low number of doses.

The fact that only a small number of instillations are necessary to obtain sustained delivery in the eye tissues of a therapeutically effective dose of antibiotic offers many advantages, in particular of convenience of treatment, and of reduction of the risk of the user possibly developing a sensitization to one of the constituents of the composition. In other words, the shorter the duration of the treatment and the more limited the number of the instillations, the more reduced the risk of reaction/irritation of the eye. The topical use has the advantage of being potentially effective against microorganisms as soon as the dose is applied, unlike the use of an oral form. In addition, the oily formulation makes it possible to obtain lachrymal, conjunctival and corneal levels greater than those obtained using aqueous suspensions.

These advantages in antibiotic efficacy in the treatment of eye diseases add to those which are rather related to the physical form of solution, as distinct from the known suspensions, or to the conditions for production, in particular regarding the convenience of sterilization. It will also be noted that the invention lends itself to using the active compounds of the macrolide family in the form of their base rather than in the salt form, which would be unavoidable for an aqueous solution, to which buffers for adjusting the pH would then have to be added.

Finally, the use of the fatty acid triglycerides according to the invention is particularly advantageous in the context of use by local application onto the eye tissues, since it makes it possible to obtain a significant time of persistence on the surface of the eye, while at the same time maintaining a risk of inflammatory reaction reduced to a minimum, due to the well-defined chemical composition of the fatty acid triglycerides and to their good capacity for solubilizing all of the active compound without, however, requiring the addition of further compounds.

The invention claimed is:

1. A pharmaceutical composition in an eye dropper for treating eye infections by local application, which is in the form of an eye lotion contained in an eye dropper, the eye lotion containing a therapeutically active content of an antibiotic macrolide compound dissolved as a true solution or as a solution that can contain particles of not more than 0.2 microns in a physiologically compatible oily vehicle of fatty acid triglycerides.

2. A pharmaceutical composition in an eye dropper according to claim 1, wherein said antibiotic compound is azithromycin at a concentration from 1 to 1.5% by weight with respect to the total weight of the composition.

3. A pharmaceutical composition in an eye dropper according to claim 1, wherein said oily vehicle is a physiologically compatible fatty oil that consists essentially of physiologically compatible triglycerides deriving from carboxylic acids of saturated hydrocarbons comprising a linear chain of medium length.

4. A pharmaceutical composition in an eye dropper according to claim 1, wherein said oily vehicle is of plant origin and comprises at least 80 % of fatty acids.

5. A pharmaceutical composition in an eve dropper for treating eye infections by local application according to claim 1, wherein the macrolide compound is an azalide compound.

6. A pharmaceutical composition for treating eye infections by local application, which is in the form of an eye lotion and comprises a therapeutically active content of azithromycin as a true solution or as a solution that can contain particles of not more than 0.2 microns within an oily vehicle made of physiologically compatible triglycerides essentially selected from triglycerides of carboxylic acids of linear-chained saturated hydrocarbons.

7. A pharmaceutical composition in an eye dropper according to claim 5, wherein said linear chains in said triglycerides are of medium length.

8. A pharmaceutical composition in an eye dropper according to claim 5, wherein said azalide compound is azithromycin at a concentration from 0.7 to 2 % by weight with respect to the total weight of the composition and wherein said triglycerides in said oily vehicle derive from carboxylic acids of linear-chained saturated hydrocarbons with a linear chain of medium length.

9. A pharmaceutical composition according to claim 6, wherein said the molecule of said linear-chained saturated hydrocarbons comprises from 5 to 12 carbon atoms.

10. A pharmaceutical composition in an eve dropper according to claim 8, wherein azithromycin is present at a concentration from 1 to 1.5 % by weight with respect to the total weight of the composition.

11. A pharmaceutical composition in an eve dropper according to claim 10, wherein said oily vehicle is made of triglycerides of caprylic acid and/or capric acid for at least 95 percent of the total weight of the oily vehicle.

12. A pharmaceutical composition in an eye dropper according to claim 2, wherein said oily vehicle has a viscosity of at least 10 mPa.s and at most 100 mPa.s at normal temperature and a density of about 1.

13. A pharmaceutical composition in an eve dropper according to claim 2, wherein said oily vehicle has a viscosity between 10 aryl 50 mPa.3 at normal temperature.

14. A pharmaceutical composition in an eye dropper according to claim 3, wherein said oily vehicle has a viscosity of about 20 to 40 mPa.s at normal temperature, a density between 0.9 and 1, and a refractive index from 1.3 to 1.5.

15. A pharmaceutical composition in an eve dropper according to claim 5, wherein said azalide compound is azithromycin at a concentration from 0.7 to 2 % by weight with respect to the total weight of the composition and wherein said oily vehicle has a viscosity between 10 and 50 mPa.s at normal temperature, a density between 0.9 and 1, and a refractive index from 1 to 2.

16. A pharmaceutical composition in the form of an eye lotion comprising a therapeutically active content of an azalide and an oily vehicle made of physiologically compatible triglycerides of carboxylic acids of linear-chained saturated hydrocarbons of medium length, wherein the azalide is present at a concentration in the range from 0.7 to 2% by weight of the total composition weight and is in true solution within said vehicle.

17. A pharmaceutical composition according to claim 6, in single-dose eye-drop bottles.

18. A pharmaceutical composition according to claim 6, containing azithromycin at a concentration from 1 to 1.5% by weight of the total composition weight.

19. A pharmaceutical composition according to claim 18, wherein said oily vehicle consists essentially of at least 95% of triglycerides of caprylic acid and/or capric acid.

20. A pharmaceutical composition according to claim 16, wherein azithromycin is present at a concentration between 1 and 1.5% by weight with respect to the total weight of the composition and said oily vehicle has a viscosity between 10 and 50 mPa.s at normal temperature, a density between 0.9 and 1, and a refractive index from 1 to 2.

21. A process for preparing a pharmaceutical eye lotion composition in an eye dropper according to claim 10 suitable for local application in ophthalmology, comprising dissolving azithromycin at a concentration between 1 and 1.5% by weight in an oily vehicle consisting essentially of pharmaceutically acceptable fatty acid triglycerides and sterilizing the solution thereby obtained by filtration through a filtering membrane with a pore size not higher than 0.2 µm.

22. A method according to claim 21, wherein said filtration is performed at normal temperature of under gentle heating up to a temperature not exceeding 80° C.

23. A pharmaceutical composition stored in an eye-drop dispenser for treating eye infections by local application, comprising a true solution or as a solution that can contain particles of not more than 0.2 microns of a therapeutically active content of azithromycin in an oily vehicle consisting essentially of triglycerides of carboxylic acids of saturated hydrocarbons with a linear chain of medium length.

24. A composition according to claim 23, wherein azithromycin is present at a concentration between 1 and 1.5% by weight with respect to the total weight of the composition.

25. A pharmaceutical composition according to claim 24, wherein said oily vehicle has a viscosity between 10 and 50 mPa.s at normal temperature, a refractive index of between 1.3 and 1.5, and a density from 0.9 to 1.

26. A pharmaceutical composition according to claim 25, stored in single-dose bottles.

27. In a method for the treatment of eye infections comprising applying onto the eye a pharmaceutical composition, the improvement wherein the pharmaceutical composition is a true solution or as a solution that can contain particles of not more than 0.2 microns of azithromycin in an oily vehicle of fatty acid triglycerides.

28. A method according to claim 27, wherein said true solution of azithromycin is at a concentration between 1 and 1.5% by weight in base form in an oily vehicle consisting essentially of triglycerides of carboxylic acids of linear-chained saturated hydrocarbons comprising from 5 to 12 carbon atoms.

29. In a method for the treatment of eye infections comprising applying to the eye a pharmaceutical composition, the improvement wherein the pharmaceutical composition comprises a true solution or as a solution that can contain particles of not more than 0.2 microns of a therapeutically effective amount of antibiotic macrolide compound dissolved in a physiologically compatible oily liquid vehicle of fatty acid triglycerides.

30. A method according to claim 29, wherein the antibiotic macrolide is an azalide compound.

* * * * *

UNITED STATES PATENT AND TRADEMARK OFFICE
CERTIFICATE OF CORRECTION

PATENT NO. : 7,064,109 B2 Page 1 of 1
APPLICATION NO. : 10/474811
DATED : June 20, 2006
INVENTOR(S) : Luyckx et al.

It is certified that error appears in the above-identified patent and that said Letters Patent is hereby corrected as shown below:

On the title page item (73), Assignee: line 1, reads "Laboratories" should read
-- Laboratoires --
Column 13, line 4, reads "eve dropper" should read -- eye dropper --
Column 13, line 27, reads "said the molecule" should read -- said molecule --
Column 13, line 29, reads "eve dropper" should read -- eye dropper --
Column 13, line 33, reads "eve dropper" should read -- eye dropper --
Column 13, line 41, reads "eve dropper" should read -- eye dropper --
Column 13, line 43, reads "aryl 50 mPa.3" should read -- and 50 mPa.s --
Column 13, line 49, reads "eve dropper" should read -- eye dropper --
Column 14, line 44, reads "or as a solution" should read -- or a solution --
Column 14, line 57, reads "or as a solution" should read -- or a solution --

Signed and Sealed this

Twenty-sixth Day of December, 2006

JON W. DUDAS
*Director of the United States Patent and Trademark Office*